US006350743B1

(12) United States Patent
Kashman et al.

(10) Patent No.: US 6,350,743 B1
(45) Date of Patent: Feb. 26, 2002

(54) CYTOTOXIC PYRIDOACRIDINE ALKALOIDS

(75) Inventors: Yoel Kashman; Ganit Koren-Goldshlager, both of Ramat Aviv (IL); Maurice Aknin, Saint-Denis Cedex (FR); Dolores Garcia Gravalos, Madrid (ES)

(73) Assignee: Instituto Biomar, S.A., Onzonilla (ES)

( * ) Notice: Subject to any disclaimer, the term of this patent is extended or adjusted under 35 U.S.C. 154(b) by 0 days.

(21) Appl. No.: 09/554,181

(22) PCT Filed: Nov. 3, 1998

(86) PCT No.: PCT/GB98/03282

§ 371 Date: Feb. 22, 2001

§ 102(e) Date: Feb. 22, 2001

(87) PCT Pub. No.: WO99/23099

PCT Pub. Date: May 14, 1999

(30) Foreign Application Priority Data

Nov. 3, 1997 (GB) .............................. 9723206

(51) Int. Cl.$^7$ ..................... A61K 31/545; C07D 513/18
(52) U.S. Cl. ................. 514/224.5; 544/14; 435/119
(58) Field of Search ................ 544/14, 224.5; 514/224.5; 435/119

(56) References Cited

U.S. PATENT DOCUMENTS 5,432,172 A * 7/1995 Spector et al. ........... 514/224.5

FOREIGN PATENT DOCUMENTS

WO  WO 00/20411   4/2000

OTHER PUBLICATIONS

Gunawardana et. al., "New Cytotoxic Acridine Alkaloids From Two Deep Water Marine Sponges Of The Family", *Tetrahedron Letters*, vol. 30, No. 33, pp. 4359–4362, 1989.
Ciufolini et. al., "A Unified Strategy for The Synthesis of Sulfer–Containing Pyridoacridine Alkaloids: Agents of Marine Origin", *J. Amer. Chem. Soc* 1995, 117, 12460–12469.

Carroll et. al., A Second Shermilamine Alkaloid From a Tunicate Trdidemnum sp. *J. Org. Chem.* 1989, 54, 4231–4232.

Schmitz et. al., "Cytotoxic Aromatic Alkaloids from the Ascidian Amphicarpa meridiana and Leptoclinides sp.: Meridine and 11–Hydroxyascididemin", *J. Org. Chem.* 1991, 56, 804–808.

Carroll et. al., "Kuanoniamines A, B, C, and D: Pentacyclic Alkaloids from a Tunicate and Its Prosobranch Mollusk Predator Chelynotus semperi", *J. Org. Chem.* 1990, 55, 4426–4431.

Gunawardana et. al., "Pyridoacridine Alkaloids from Deep–Water Marine Sponges of the Family Pachastrellidae: Structure Revision of Dercitin and Related Compounds and Correlation with the Kuanoniamines", *J. Org. Chem.* 1992, 57, 1523–1526.

\* cited by examiner

*Primary Examiner*—Richard L. Raymond
(74) *Attorney, Agent, or Firm*—Ernest V. Linek; Banner & Witcoff, Ltd.

(57) ABSTRACT

Shermilamine D, a novel cytotoxic pyridoacridine alkaloid of Formula 1, (1)

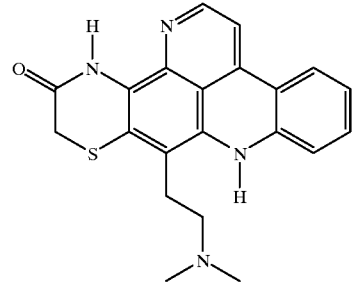

has been isolated from the tunicate *Cystodytes violatinctus*. The structure of the compound has been established on the basis of 1-D and 2-D NMR data.

9 Claims, No Drawings

CYTOTOXIC PYRIDOACRIDINE ALKALOIDS

CROSS-REFERENCE TO RELATED APPLICATIONS

The present invention is a Section 371 filing of PCT/GB98/03282 filed Nov. 3, 1998, which designated the United States. The PCT application was published in the English language on May 14, 1999. Priority was claimed from Application No. 9,723206.0 filed Nov. 3, 1997 in Great Britain.

The present invention relates to new cytotoxic pyridoacridine alkaloids, one of which, Shermilamine D, isolated from the tunicate Cystodytes violatinctus.

BACKGROUND OF THE INVENTION

Marine organisms, especially soft cerals, sponges and tunicates, provide many secondary metabolites and exhibit a varying degree of biological activity (Reference 13: Faulkner, D. J. Nat.Prod.Reports., 1997, 14, 259–302 and references cited therein). An important family of these metabolites is the alkaloid family; in 1983 it was reported the structure of a marine alkaloid, amphimedine (Reference 14: Schmitz, F. J. et al. J.Am.Chem.Soc. 1983, 105, 4835–4836), which was the first of a new class of marine-derived alkaloids that collectively have come to be known as the "pyridoacridines". Since then, over 40 additional examples have been published (Reference 1: Molinski, T. F. Chem.Rev. 1993, 93, 1825–1838). The pyridoacridines are highly colored marine derived alkaloids majority based on the 11H-pyrido[4,3,2-mn]acridine skeleton, as shown below:

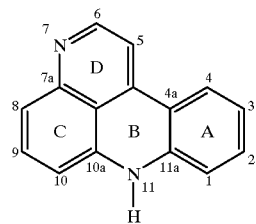

11H-pyrido[4,3,2-mn]acridine skeleton

A family of remarkable cytotoxic marine pyridoacridine alkaloids is the Shermilamine family (Reference 6: Scheuer, P. J. et al. J.Org.Chem. 1988, 53, 4619–4620. Reference 5: Scheuer, P. J. et al. J.Org.Chem. 1989, 54, 4231–4232. Reference 3: Kashman, Y. et al. J.Org.Chem. 1989, 54, 5335–5337. Reference 12: Barrows, L. R.; Ireland, C. M. et al, J.Med.Chem. 1994, 37, 3819–3827), which structure is showed below:

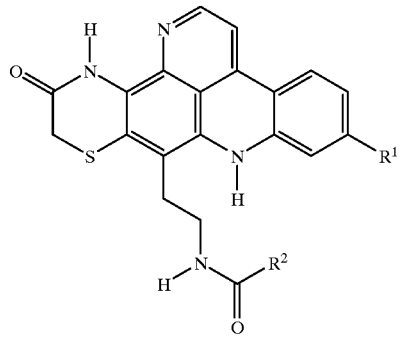

Shermilamine A: $R^1$=Br $R^2$=(CH$_3$)
Shermilamine B: $R^1$=H $R^2$=(CH$_3$)
Shermilamine C: $R^1$=H $R^2$=(CH=C(CH$_3$)$_2$)

Shermilamines were all isolated from tunicates, A and B from *Trididemnum sp.* and C from *Cystodytes sp.*

SUMMARY OF THE INVENTION

The present invention provides new pyridoacridines having the following formula (I):

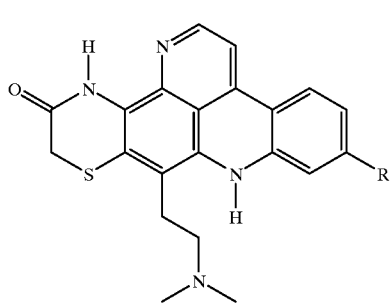

I wherein R is independently selected from the group consisting of hydrogen or bromine.

More particularly, the present invention relates to Shermilamine D (R=H in formula (I)), extracted and isolated from the tunicate *Cystodytes violatinctus*.

Shermilamine D exhibits antitumor activity. In particular, Shermilamine D exhibits antitumor activity against cell lines derived from human solid tumors, such as human lung carcinoma, human colon carcinoma and human melanoma, and, the like, it is active against other tumor cell lines, like leukemia and lymphoma.

The present invention also provides a method of testing a mammal affected by a malignant tumor sensitive to a compound with the formula (I), which comprises administering a therapeutically effective amount of the compound with the formula (I), or a pharmaceutical composition thereof.

The present invention further provides pharmaceutical compositions which contain as active ingredient a compound with the formula (I), as well as process for its preparation.

A further aspect of the invention is a method for preparing the compound Shermilamine D (R=H in the formula (I)), which comprises extraction and isolation from the tunicate *Cystodytes violatinctus*.

PREFERRED EMBODIMENTS OF THE INVENTION

Examples of pharmaceutical compositions include any solid (tablets, pills, capsules, granules, etc.) or liquid (solutions, suspensions or emulsions) with suitable formulation of oral, topical or parenteral administration, and they may contain the pure compound or in combination with any carrier or other pharmacologically active compounds. These compositions may need to be sterile when administered parenterally.

The correct dosage of a pharmaceutical composition comprising compounds with the formula (I), will vary according to the pharmaceutical formulation, the mode of application, and the particular situs, host and tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

ANTITUMOUR ACTIVITY

Cells were maintained in logarithmic phase of growth in Eagle's Minimum Essential Medium, with Earle's Balanced Salts, with 2.0 mM L-glutamine, with non-essential amino acids, without sodium bicarbonate (EMEM/neaa); supplemented with 10% Fetal Calf Serum (FCS), $10^{-2}$ M sodium bicarbonate and 0.1 g/l penicillin+G streptomycin sulfate.

A screening procedure has been carried out to determine and compare the antitumor activity of these compounds, using an adapted form of the method described by Bergeron et al. (Reference 15: Raymond J. Bergeron, Paul F. Cavanaugh, Jr., Steven J. Kline, Robert G. Hughes, Jr., Gary T. Elliot and Carl W. Porter. Antineoplastic and antiherpetic activity of spermidine catecholamide iron chelators. *Biochem. Bioph. Res. Comm.* 1984, 121, 848–854). The antitumor cells employed were P-388 (suspension culture of a lymphoid neoplasm from DBA/2 mouse), A-549 (monolayer culture of a human lung carcinoma), HT-29 (monolayer culture of a human colon carcinoma) and MEL-28 (monolayer culture of a human melanoma).

P-388 cells were seeded into 16 mm wells at $1 \times 10^4$ cells per well in 1 ml aliquots of MEM 5FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, an approximately $IC_{50}$ was determined by comparing the growth in wells with drug to the growth in wells control.

A-549, HT-29 cells were seeded into 16 mm wells at $2 \times 10^4$ cells per well in 1 ml aliquots of MEM 10FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, the wells were stained with 0.1% Crystal Violet. An approximately $IC_{50}$ was determined by comparing the growth in wells with drug to the growth in wells control.

The results were given in the following table:

|  | $IC_{50}$ ($\mu$M) | | | |
|---|---|---|---|---|
|  | P-388 | A-549 | HT-29 | MEL-28 |
| Shermilamine D | 1.33 | 0.27 | 2.66 | 0.53 |

EXTRACTION AND ISOLATION

Low-resolution mass spectra were recorded on a EIMS mass spectrometer. H and $^{13}$C-NMR spectra were recorded on a Bruker ARX-500 spectrometer. All chemical shifts were reported with respect to TMS ($\delta$=0 ppm).

The tunicate *Cystodytes violatinctus* was collected by SCUBA at 5 m depth on Prevoyante reef in lagoon of Mayotte (Comoros islands), north-west of Madagascar during April 1996. Reference samples (AM-35) are deposited at the Museum National d'Histoire Naturelle of Paris. The freshly collected animals was immediately frozen at −25° C. The freeze-dried animal (600 g weight after extraction) were homogenized and extracted with methanol-chloroform 1:2 (500 ml×4) at room temperature. The extracts were evaporated into vacuto to give an aqueous phase wich was extracted with chloroform. Evaporation of the chloroform extracts afforded an oily residue (1.6 g). The crude extract is partitioned between 20% aq. MeOH and $CCL_4$, the organic extracts were evaporated and the residue is then chromatographed, first on Sephadex LH-20 (hexane, $CHCl_3$, MeOH, 2:1:1) and then MeOH-washed-silica-gel chromatography starting with $CHCl_3$ and adding MeOH, 1–10%. The compound Shermilamine D (2% from the crude extract) comes out with 5% MeOH in $CHCl_3$. Shermilamine D is a foaming oil, m/z 376 ($C_2H_{20}N_4OS$).

For NMR data see next Table:

| NMR data for Shermilamine D | | | |
|---|---|---|---|
| C No. | $\delta_C$(m)$^a$ | $\delta_H$(m, J in Hz)$^{a,b}$ | HMBC to C No. |
| 2 | 150.7(d) | 8.40(d, 4.8) | 3,3a,13b |
| 3 | 106.8(d) | 7.20(d, 4.7) | 2,8b |
| 3a | 140.2(s) | — | — |
| 3b | 116.3(s) | — | — |
| 4 | 123.7(d) | 7.80(d, 7.9) | 3b,6,7a |
| 5 | 120.6(d) | 6.98(t, 7.5) | 3a,3b,6,7 |
| 6 | 131.7(d) | 7.33(bt, 7.5) | 4,7a |
| 7 | 116.4(d) | 6.84(d, 8.1) | 3b,5 |
| 7a | 140.7(s) | — | — |
| 8a | 132.9(s) | — | — |
| 8b | 116.7(s) | — | — |
| 9 | 109.6(s) | — | — |
| 9a | 121.4(s) | — | — |
| 11 | 29.7(t) | 3.50(bs) | 9a,12 |
| 12 | 163.5(a) | — | — |
| 13a | 121.3(s) | — | — |
| 13b | 137.3(s) | — | — |
| 14 | 27.4(t) | 2.96(bt, 4.0) | 8a,9a,15,17,18 |
| 15 | 58.7(t) | 2.62(bt, 4.8) | 14,17,18 |
| 17 | 44.9(q) | 2.50(s) | 15,18 |
| 18 | 44.9(q) | 2.50(s) | 15,17 |
| NH-8 | — | 10.2(bs) | — |
| NH-13 | — | 9.05(bs) | 9a.11.13b | aNMR solvent = $CDCl_3$; 500 MHz for $^1$H, 125 MHz for $^{13}$C.
bNMR solvent = $CDCl_3$—$CD_3OD$ (4:1).

REFERENCES

1. Molinski T. F. *Chem.Rev.* 1993, 93, 1825–1838.
2. Scheuer, P. J. et al, *J.Org.Chem.* 1990, 55, 4426–4431.

3. Kashman, Y. et al, *J.Org.Chem.* 1989, 54, 5335–5337.
4. Schmitz, F. J.; Helm, D. v. d. *J.Org.Chem.* 1991, 56, 804–808.
5. Scheuer, P. J. et al. *J.Org.Chem.* 1989, 54, 4231–4232.
6. Scheuer, P. J. et al. *J.Org.Chem.* 1988, 53, 4619–4620.
7. Steffan, B. et al. *Tetrahedron,* 1993, 49, 6223–6228.
8. Spector, I. et al. *J.Cell.Physiol.* 1993, 157, 481–492.
9. Burres, N. S. et al. *Cancer Res.* 1989, 49, 5267–5274.
10. Ciufolini, M. A. et al. *J.Am.Chem.Soc.* 1995, 117, 12460–12469.
11. Taraporewala, I. B. et al. *J.Med.Chem.* 1992, 35, 2744–2752.
12. Barrows, L. R.; Ireland, C. M. et al. *J.Med.Chem.* 1994, 37, 3819–3827.
13. Faulkner, D. *J.Nat.Prod.Reports,* 1974, 14, 259–302.
14. Schmitz, F. J. et al. *J.Am.Chem.Soc.* 1983, 105, 4825–4836.
15. Raymond J. Bergeron, Paul F. Cavanaugh, Jr, Steven J. Kline, Robert G. Hughes, Jr., Gary T. Elliot and Carl W. Porter, Antineoplastic and antiherpetic activity of spermidine catechloamide iron chelators. *Biochem. Bioph. Res. Comm.* 1984, 121, 848–854.

What is claimed is:

1. A compound having the following formula (I):

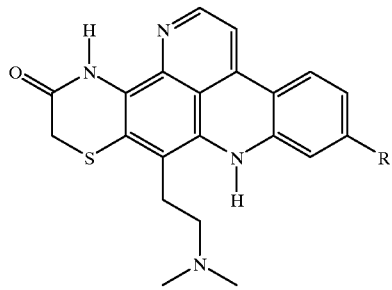

I wherein R is independently selected from the group consisting of hydrogen or bromine.

2. A compound, Shermilamine D, according to claim 1, having the following formula:

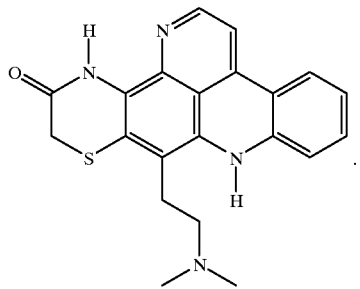

Shermilamine D

3. A method of treating a mammal affected by a malignant tumor sensitive to a compound with the formula (I), as defined in claim 1, which comprises administering to the affected individual a therapeutically effective amount of the compound or a pharmaceutical composition thereof.

4. A method of treating a mammal affected by a malignant tumor sensitive to Shermilamine D, as defined in claim 2, which comprises administering to the affected individual a therapeutically effective amount of Shermilamine D or a pharmaceutical composition thereof.

5. A pharmaceutical preparation which contains as active ingredient a compound with the formula (I), as defined in claim 1.

6. A pharmaceutical preparation which contains as active ingredient Shermilamine D, as defined in claim 2.

7. (Amended) A method of treating a mammal affected by a malignant tumor which comprises administering to the affected individual a therapeutically effective amount of a compound with the formula (I), as defined in claim 1, together with one or more other antitumoral compounds.

8. (Amended) A method of treating a mammal affected by a malignant tumor which comprises administering to the affected individual a therapeutically effective amount of Shermilamine D, as defined in claim 2, together with one or more other antitumoral compounds.

9. A method for preparing Shermilamine D, as defined in claim 2, which comprises extraction and isolation from the tunicate *Cystodytes violatinctus*.

* * * * *